(12) United States Patent
Qian et al.

(10) Patent No.: US 9,476,075 B2
(45) Date of Patent: Oct. 25, 2016

(54) **OIL ENRICHED WITH ARACHIDONIC ACID OF MICROORGANISMS (UNICELLULAR FUNGUS *MORTIERELLA ALPINA*) AND METHOD FOR THE PRODUCTION THEREOF**

(71) Applicant: ROQUETTE FRERES, Lestrem (FR)

(72) Inventors: Yun Qian, Wuhan (CN); Jie Zhou, Wuhan (CN); Bernard Pora, Wuhan (CN)

(73) Assignee: ROQUETTE FRERES, Lestrem (FR)

( * ) Notice: Subject to any disclaimer, the term of this patent is extended or adjusted under 35 U.S.C. 154(b) by 0 days.

(21) Appl. No.: 14/428,077

(22) PCT Filed: Sep. 12, 2013

(86) PCT No.: PCT/FR2013/052092
§ 371 (c)(1),
(2) Date: Mar. 13, 2015

(87) PCT Pub. No.: WO2014/041303
PCT Pub. Date: Mar. 20, 2014

(65) Prior Publication Data
US 2015/0252395 A1     Sep. 10, 2015

(30) Foreign Application Priority Data
Sep. 14, 2012 (CN) .......................... 2012 1 0343057

(51) Int. Cl.
| | | |
|---|---|---|
| *C12P 7/64* | (2006.01) | |
| *A23D 9/00* | (2006.01) | |
| *C11B 1/04* | (2006.01) | |
| *C11B 1/10* | (2006.01) | |
| *C12R 1/645* | (2006.01) | |
| *C12N 1/14* | (2006.01) | |
| *A23L 1/30* | (2006.01) | |
| *A23L 1/28* | (2006.01) | |

(52) U.S. Cl.
CPC ............... *C12P 7/6427* (2013.01); *A23D 9/00* (2013.01); *A23K 10/12* (2016.05); *A23K 50/30* (2016.05); *A23K 50/40* (2016.05); *A23K 50/80* (2016.05); *A23L 1/28* (2013.01); *A23L 1/3008* (2013.01); *C11B 1/04* (2013.01); *C11B 1/10* (2013.01); *C12N 1/14* (2013.01); *C12R 1/645* (2013.01); *A23V 2002/00* (2013.01)

(58) Field of Classification Search
None
See application file for complete search history.

(56) References Cited

FOREIGN PATENT DOCUMENTS

| | | |
|---|---|---|
| EP | 0 956 774 | 11/1999 |
| EP | 1 035 211 | 9/2000 |
| WO | WO 2004/084882 | 10/2004 |

OTHER PUBLICATIONS

Nisha et al. "Effect of culture variables on mycelial arachidonic acid production by Mortierella alpine". Food and Bioprocess Technology, 2011, 4(2), pp. 232-240.*
Sakuradani, E. et al. "Improvement of arachidonic acid production by mutants with lower n-3 desaturation activity derived from *Mortierella alpina* 1S-4" *Appl Microbiol Biotechnol*, Aug. 5, 2004, pp. 243-248, vol. 66, No. 3.
Shinmen, Y. et al. "Production of arachidonic acid by *Mortierella* fungi" *Appl Microbiol Biotechnol*, Jul. 1989, pp. 11-16, vol. 31.
Certik, M. et al. "Desaturase-defective fungal mutants: useful tools for the regulation and overproduction of polyunsaturated fatty acids" *Trends in Biotechnology*, Dec. 1998, pp. 500-505, vol. 16, No. 12.
Database EMBL [Online] Accession No. EM_STD:KC018320, "Mortierella alpine strain CBS 529.72 28S ribosomal RNA gene, partial sequence." Jun. 18, 2013, p. 1, XP-002716228.
Database CBS, Accession No. 529.72. Taxon name: Mortierella alpina Peyronel, I germi astmosferici dei fungi con micelio: 17 (1913) [MB#170280], Oct. 29, 2013, p. 1, XP-002716227.

* cited by examiner

*Primary Examiner* — Vera Afremova
(74) *Attorney, Agent, or Firm* — Saliwanchik, Lloyd & Eisenschenk

(57) ABSTRACT

The invention relates to a strain of *Mortierella alpina* that can produce large quantities of arachidonic acid (ARA), to the methods for producing lipidic compounds of interest using said strain, and to the products and compositions produced with said strain.

6 Claims, No Drawings

OIL ENRICHED WITH ARACHIDONIC ACID OF MICROORGANISMS (UNICELLULAR FUNGUS *MORTIERELLA ALPINA*) AND METHOD FOR THE PRODUCTION THEREOF

CROSS-REFERENCE TO RELATED APPLICATION

This application is the U.S. national stage application of International Patent Application No. PCT/FR2013/052092, filed Sep. 12, 2013.

The Sequence Listing for this application is labeled "Seq-List.txt" which was created on Mar. 9, 2015 and is 1 KB. The entire content of the sequence listing is incorporated herein by reference in its entirety.

The present invention relates to a novel composition of oil rich in arachidonic acid, said oil being produced by a microorganism, preferentially produced by a single-cell fungus (filamentous mold) of the *Mortierella* genus, in this case a particular strain of *Mortierella alpina*.

Lipids constitute one of the three major families of macronutrients with proteins and carbohydrates.

Among lipids, triglycerides and phospholipids in particular stand out.

Triglycerides represent approximately 95% of ingested food lipids. In the organism, they are principally present in adipose tissues and constitute the principal energy storage form.

Phospholipids are structural lipids since they are constituents of cell membranes for which they provide, inter alia, the fluidity.

Triglycerides and phospholipids are predominantly composed of fatty acids which are both provided by the diet and, for some of them, synthesized by the organism.

The biochemical classification (based on the number of double bonds contained in the fatty acid molecule) distinguishes saturated fatty acids (SFAs), monounsaturated fatty acids (MUFAs) and polyunsaturated fatty acids (PUFAs).

From a physiological point of view, the following are distinguished:
  indispensable fatty acids, required for development and correct functioning of the human body, but which our bodies are not able to produce;
  "conditionally" indispensable fatty acids, which are essential for normal growth and the physiological functions of cells, but which can be produced from their precursor if it is provided by the diet, and are therefore rigorously required if their indispensable precursor is absent; and
  non-indispensable fatty acids.

The set of indispensable and "conditionally" indispensable fatty acids constitutes the essential fatty acids.

The other fatty acids are termed non-essential.

Two major families of essential fatty acids are distinguished: the omega 6 fatty acids (or n-6 PUFAs), of which the precursor and the major representative is linoleic acid (LA), and the omega 3 fatty acids (or n-3 PUFAs), of which the precursor is alpha-linolenic acid (ALA).

Among the non-indispensable fatty acids are, in particular:
  eicosapentaenoic acid (EPA) of the omega 3 fatty acid family,
  oleic acid, a predominant monounsaturated fatty acid in our diet, and
  saturated fatty acids.

In addition to their production from peanuts, safflower, rapeseed, corn, flax, hazelnut, sesame, soybean or sunflower, a large variety of polyunsaturated fatty acids can be produced by various single-cell organisms (algae, fungi, etc.).

Arachidonic acid ("ARA") is a long-chain fatty acid that is found in certain vegetable oils.

It is a C 20:4 (n-6, n-9, n-12, n-15) polyunsaturated fatty acid, i.e., a fatty acid containing 20 carbon atoms and four ethylenic bonds located on carbon atoms no. 5 (n-15), no. 8 (n-12), no. 11 (n-9) and no. 14 (n-6).

It is a fatty acid which is also termed "tetraenoic" since it has four unsaturations (four carbon-carbon double bonds).

It is also found in the literature under the name "all-cis-5,8,11,14-eicosatetraenoic" ("cis" defining the configuration of the double bonds, all the double bonds being in the "cis" configuration).

ARA is one of the most abundant C20 PUFAs in the human body, where it is produced from linoleic acid.

It is found in the organs, the muscles and the blood.

ARA is an important precursor of a large variety of biologically active compounds, known collectively as "eicosanoids", a group comprising prostaglandins, thromboxanes and leukotrienes.

These eicosanoids exhibit regulatory effects on lipoprotein metabolism, blood rheology, muscle tone, leukocyte function, platelet activation and cell growth.

ARA is also one of the components of the lipid fraction of human maternal milk and is considered to be essential for optimal neurological development in infants.

In their efforts to obtain preparations for infants corresponding to the long-chain fatty acid profile of maternal milk, scientists and food regulating organizations have recommended that arachidonic acid be added to infant preparations, in particular in the formula used for premature babies.

In particular, it is preferable for the oil containing arachidonic acid produced for use in infant preparations to contain few or no other PUFAs (for example, eicosapentaenoic acid or EPA).

These other PUFAs are not recommended because some of these fatty acids can interfere with the use of arachidonic acid as such by the child, and/or can impair the mixing of the oil containing arachidonic acid with other oils in order to achieve the appropriate ratio of fatty acids of maternal milk (reconstituted maternal milk) or for other desired applications.

Moreover, ARA has a great variety of applications, such as use in preparations for food products for humans, as well as animal feeds.

ARA has several properties recognized in animal feed:
  anti-inflammatory properties, since ARA is a precursor of series II prostaglandins and of anandamide (mainly demonstrated on pigs),
  anti-stress properties in fish (sea bream) via means other than prostaglandins, and
  immunomodulatory properties in pigs.

Transfer studies have also been carried out in order to visualize the passage of arachidonic acid into the meat, the milk or the eggs produced.

When it is isolated from microorganisms, the commercial product is in particular available in the form of an arachidonic acid-rich oil obtained by means of the fermentation of filamentous molds of the *Mortierella* genus.

In EP 276541, a process for the production of ARA by *Mortierella elongata*, *Mortierella exigua* and *Mortierella hygrophila* is thus described.

International patent application WO 94/28913 describes, for its part, a fermentative process using *Mortierella alpina* for producing ARA substantially devoid of EPA.

However, as is confirmed in EP 726 321, of all the *Mortierella* tested for their ARA production (*alpina, hygrophila, spinosa, schmuckeri* and *carmagensis*), it is the strains of *Mortierella schmuckeri* or *Mortierella carmagensis* which exhibit the most advantageous productivity.

It is therefore accepted by specialists in the field of ARA production that it is through the choice of a strain of *M. schmuckeri* or *M. carmagensis*, to the detriment of *M. alpina, hygrophila* or *spinosa*, that it is possible to guarantee better yields, productivity and quality.

However, there remains a need to have alternative means for producing quality oils which have a high ARA content and which have entirely specific long-chain saturated or polyunsaturated fatty acid profiles.

Moreover, for many national regulatory authorities, only *Mortierella alpina* is authorized in infant food.

It has first of all been to the credit of the applicant company to provide a novel composition of oil, enriched with arachidonic acid, which has:
  low contents of polyunsaturated fatty acids other than ARA (such as EPA), and
  a limited content of certain long-chain saturated fatty acids (such as behenic acid, myristic acid, palmitic acid or lignoceric acid).

It has moreover been noted by the applicant company that the low content of these saturated fatty acids makes it possible to obtain an oil of better quality than those that are commercially available, in terms of clearness and low turbidity when cold.

Concerned with developing a production process which is much more efficient and much less expensive than those described in the prior art, the applicant company has, during its research, identified a novel strain of *Mortierella alpina* which has an exceptional capacity for producing arachidonic acid since it allows a production reaching more than 50% of arachidonic acid (the % being understood here to be by weight of total fatty acids).

The applicant company has therefore been up against a technical bias, which aims to seek, in the strains of the *M. schmuckeri* or *M. carmagensis* type, the best ARA-producing strains.

Moreover, in addition to the notable capacity for producing arachidonic acid, this strain also makes it possible to obtain (the % are understood here to be by weight of total fatty acids):
  less than 0.5%, preferably less than 0.2% of EPA,
  less than 0.5%, preferably less than 0.2% of myristic acid (C14:0),
  less than 9%, preferably less than 7% of palmitic acid (C16:0),
  less than 3%, preferably less than 2.5% of behenic acid (C22:0), and
  less than 3%, preferably less than 2.5% of lignoceric acid (C24:0).

This *Mortierella alpina* strain was filed in France on Jun. 12, 2012, with the Collection Nationale de Cultures de Microorganismes [National Microorganism Culture Collection] of the Institut Pasteur (CNCM) under number CNCM I-4642, and also in China with the China Center for Type Culture Collection (CCTCC) of Wuhan University, Wuhan 430072, P. R. China under number M 209116.

It has been characterized by sequencing the D1-D2 region of the gene encoding the 25S RNA (SEQ ID NO: 1):

```
  1 TTAAACAGTG CGTGAAATTG TTGAAAGGGA AACGCTTGAC
    ACCAGTCATG CGAGCGGAAA

61 ATCAGTCTTT TGCAGTGGGG AGTTGTGTGG GTTCGGACCG
    CAAGGCCGGC CTGTGCTGCA

121 TCTCTGCTGT AAGTGATGCA CTTTTTCGTT TGCAGGCCAA
    CATCAGTTTC TTCTGCTGGA

181 CAAAACTCTT GAGAAGGTAG CAGCTTTGGC TGTGTTATAG
    CTCTTGAGCG ATACAGTGGA

241 GGGGACTGAG GTTTTCGCAG CGCGTGCTCT CGGGCAAGGC
    TGATTGGGTG CTATGGGATC

301 GTTCGGTGTA CAATGCATGC ATTTTGCGCC GTGTCTTTTC
    TGTACTCGCT CAACTCGGCT

361 C
```

This has made it possible to identify it as being a strain of the *Mortierella alpina* type.

Consequently, the present invention relates to the *Mortierella alpina* strain filed on Jun. 12, 2012, with the CNCM under number I-4642.

This strain may subsequently be denoted "CNCM I-4642" in the present application.

The present invention also relates to a variant of this strain or a strain derived from said strain, said variant or said derived strain retaining the property of producing high arachidonic acid contents. In particular, it allows the production of ARA with a minimum of 50% of arachidonic acid by weight of total fatty acids.

In particular, the present invention relates to a *Mortierella alpina* strain obtained from the CNCM I-4642 strain by mutagenesis or by gene transformation. The mutagenesis may be site-directed and/or random.

The present invention also relates to a method for preparing such a strain, comprising the mutagenesis or gene transformation of the CNCM I-4642 strain and, optionally, a screening step which makes it possible to select the strains producing at least 50% of arachidonic acid by weight of total fatty acids.

The invention relates to a method for culturing the CNCM I-4642 strain or a variant or strain derived from said strain which retains the capacity for producing arachidonic acid, comprising a step of culturing said strain in an appropriate medium and under suitable fermentation conditions.

The invention relates, moreover, to a method for preparing arachidonic acid in the form of an oil extracted from the CNCM I-4642 strain or from a variant or strain derived from said strain, characterized in that the oil containing the arachidonic acid is prepared by means of a method comprising:
  culturing the strain under heterotrophic conditions so as to produce a biomass having between 40% and 55% by weight of lipids, preferentially between 40% and 50% by weight of lipids, even more preferentially about 45% by weight of lipids and between 50% and 55% by weight of ARA relative to the weight of total fatty acids,
  harvesting the biomass thus prepared,
  drying said biomass,
  extracting the oil with a solvent chosen from the group consisting of hexane and butane, more particularly with liquid butane, and
  refining and recovering the oil thus extracted.

Optionally, the biomass resulting from the step of extracting the oil can itself be recovered and exploited in animal feed (as a feed supplement for farm animals (pigs, etc.), pets, and in aquaculture).

The culturing is carried out under heterotrophic conditions. Generally, the culturing step comprises a preculturing step, to revive the strain, and then a step of actual culturing or fermentation. The latter step corresponds to the step for producing the lipid compounds of interest.

The applicant company recommends, for the CNCM I-4642 strain, carrying out a five-step aerobic fermentation, as will be identified hereinafter.

The first four steps are characterized by culturing the CNCM I-4642 strain in a medium in which the provision of carbon source is regulated according to the kinetics of production of the biomass, the total lipids and the arachidonic acid.

In these four steps, it should be noted that, contrary to other processes of the prior art for producing arachidonic acid by fermentation of *Mortierella*, the supply of carbon source is not or is barely limiting with regard to the growth of the microorganism.

On the other hand, during the fifth step, the culture medium has a low concentration of carbon source, at most 1% by weight, and the supply of carbon source is even stopped.

In this step, the carbon source becomes limiting for the growth of the microorganism, or is limited such that the microorganisms are led to metabolize their own fats and/or lipids.

It is important to note that, contrary to what is described in the literature:
- There is no need here to regulate/control the dissolved oxygen concentration in the culture medium, but rather to keep it at the maximum. There is therefore no regulation here in terms of oxygen provision in order to increase ARA production.
- There is also no need to precisely define phosphate, potassium, sodium, magnesium and calcium provisions in the culture medium, in particular for controlling the morphology of the microorganism's mycelium during fermentation.

The present invention subsequently relates to the recovery, at the end of fermentation, of the biomass rich in lipid compounds of interest, in this case ARA.

After the fermentation step, the biomass may be:
- pasteurized, so as to inactivate the lipid-degrading enzymes (lipases) present in the biomass as such, but also in the culture medium,
- recovered from the fermentation medium by any method known per se to those skilled in the art; for example, the biomass may be extracted from the fermentor and simply concentrated by microfiltration or centrifugation, or washed via a succession of concentrations-dilutions with an aqueous solution.

The invention thus relates to the biomass comprising the CNCM I-4642 strain or a variant or a strain derived from said strain which retains the capacity for producing ARA.

Quite particularly, after the fermentation or culturing step, this biomass is rich in lipid compounds of interest such as ARA.

It can be obtained by means of the method described in the present document.

After fermentation, the biomass may contain:
- between 40% and 55% by weight of lipids relative to the total weight of the biomass, preferentially between 40% and 50% by weight of lipids, even more preferentially about 45% by weight of lipids, and
- between 50% and 55% by weight of ARA relative to the weight of total fatty acids.

In addition to the biomass, the present invention also relates to a cell extract or lysate prepared from this biomass comprising the CNCM I-4642 strain or a variant or a strain derived from said strain which retains the capacity for producing ARA.

In particular, this extract or lysate is prepared from the biomass recovered after fermentation.

This extract or lysate is then rich in lipid compounds of interest such as ARA. In particular, it may contain between 40% and 55% by weight of lipids, preferentially between 40% and 50% by weight of lipids, even more preferentially about 45% by weight of lipids and between 50% and 55% by weight of ARA relative to the weight of total fatty acids.

The rupturing of the cells for the extraction of the lipid content can be carried out by various routes, among which are mechanical, chemical and enzymatic routes.

The present invention also relates to the oil extracted from the biomass with a solvent chosen from the group consisting of hexane and butane, more particularly with liquid butane, in particular in several successive extractions.

The oil can be recovered after vacuum distillation.

However, preferentially, the oil is recovered after two refining and purification phases.

The refining phase comprises six successive steps conventionally carried out by those skilled in the art:
- degumming: acidification with citric acid,
- saponification: neutralization with alkalis,
- centrifugation to remove the gums and soaps,
- washing with water,
- discoloring with siliceous earth, active carbon and clay, and
- filtration.

The objective of the purification phase is to remove bad tastes and peroxides, and it optimizes the stability of the oil.

This phase successively comprises one or two steps of:
- molecular distillation (used if the content of unsaponifiables (UNS factor) is too high), and
- vapor deodorization under strong vacuum.

As will be exemplified hereinafter, the applicant company also recommends recovering the volatile fraction resulting from the step of vapor deodorization under strong vacuum.

Indeed, this fraction consists of at least 80% of triglycerides (the fatty acid distribution of which is comparable to that of the refined ARA oil) and contains about 10% of squalene.

Thus, the method for producing ARA comprises:
- harvesting the biomass,
- drying the biomass or preparing the cell lysate,
- extracting the oil, and
- refining and purifying the oil.

The oil is extracted from the dry microbial biomass originating from a pasteurized fermentation broth.

The biomass is harvested and dried, and then the oil is extracted from the dry biomass using, for example, liquid butane as solvent.

The residual biomass is recovered, dried and conditioned for animal feed applications.

Finally, the oil contains at least 50% of ARA and at least 90% of triglycerides relative to the weight of total acids.

The present invention relates to the use of the ARA or of the ARA-rich oil produced by any one of the processes of the present invention in the preparation of compounds intended for the food sector, in particular infant food.

Thus, it relates to a method for preparing compositions intended for the food sector, comprising the production of ARA or of ARA-rich oil by any one of the processes of the present invention, then the preparation of compositions intended for the food sector by adding said ARA or ARA-rich oil.

The present invention relates in particular to a product or a composition comprising the CNCM I-4642 strain or a variant or a strain derived from said strain which retains the capacity for producing ARA, a biomass obtained by culturing or fermenting said strain, or a cell extract or lysate thereof. It also relates to a product or composition comprising ARA-rich oil produced by any one of the processes of the present invention. Said product or composition is rich in lipid compounds of interest, such as arachidonic acid (ARA). In particular, said product or composition is rich in ARA. Preferably, it comprises more than 50% of arachidonic acid (ARA) by weight relative to total fatty acids. In addition, it contains:

- less than 0.5%, preferably less than 0.2% of EPA,
- less than 0.5%, preferably less than 0.2% of myristic acid (C14:0),
- less than 9%, preferably less than 7% of palmitic acid (C16:0),
- less than 3%, preferably less than 2.5% of behenic acid (C22:0), and
- less than 3%, preferably less than 2.5% of lignoceric acid (C24:0).

Preferably, this product or composition is a food composition or a food or nutritional supplement.

It may be in liquid or solid form.

In particular, the product may contain a cell lyophilisate or cell extract or lysate thereof.

This product or composition may be in powder, granule, gel capsule, capsule or tablet form, preferably in powder form.

Alternatively, the product or composition is in liquid form and comprises the crude or refined oil obtained by any one of the processes of the present invention.

With regard to the residual biomass resulting from the oil extraction step, it has a composition that is entirely suitable for its purpose in animal feed, as will be exemplified hereinafter.

The invention will be understood more clearly from the examples which follow, which are intended to be illustrative and nonlimiting.

EXAMPLE 1

Production of an ARA-Rich Crude Oil by the *Mortierella alpina* Strain CNCM I-4642

The principal fermentation is carried out in fermentors containing culture media inoculated from two series of smaller fermentors:

Rapid Preculture (6×200 ml)
in a medium containing 3% of glucose, 1.5% of yeast powder (7% nitrogen content),
temperature of 28° C.,
stirring at 240 rpm,
duration of 24-48 hours.
At the end of this preculture, the 6×200 ml are mixed together in a 3 l reactor.

First Fermentation Step (1 m³ Reactor)
in a medium containing 3% of glucose, 1.5% of yeast powder (7% nitrogen content),
amount of inoculum: 0.1 to 1 vol %,
temp.: 28° C.,
pressure: 0.03 mPa,
degree of aeration: maximum,
no mechanical stirring,
duration: 32 to 48 h,
working volume: 70% of the total volume,
pH: 6 to 6.5 (adjusted with alkalis),
final volume: 750 l.

Second Fermentation Step (10 m³ Reactor)
in a medium containing 4% of glucose, 1.5% of yeast powder (7% nitrogen content), 0.2% of antifoam (sunflower oil),
amount of inoculum: 10 to 15 vol %,
temp.: 28° C.,
pressure: 0.03 mPa,
degree of aeration: maximum,
no mechanical stirring,
duration: 24 to 32 h,
working volume: 70% of the total volume,
pH: 6 to 6.5 (adjusted with alkalis),
final volume: 7.5 m³.

Principal Fermentation (85 m³ Reactor)
in a medium containing 3% of glucose, 2% of yeast powder (7% nitrogen content), 0.2% of sunflower oil,
C/N (carbon/nitrogen) ratio: 7 to 8,
amount of inoculum: 15 to 25 vol %,
temp.: 27-28° C.,
degree of aeration: maximum,
no mechanical stirring,
duration: 155 to 165 h,
working volume: 70% of the total volume,
pH: 7-7.1,
final volume: 60-63 m³.

If endeavoring to describe this principal fermentation step, what is retained is that it is in this case an aerobic fermentation process.

The fermentation reactor is defined in such a way as to carry out the aeration and mixing of the cells and the culture medium without mechanical means: it is preferably in this case a bubble column having a diameter of 3.5 m and a height of 8.7 m.

The total volume of the fermentor is 85 m³. The fermentation generally lasts 6 to 7 days (155 to 165 hours) and the temperature is from 27 to 28° C.

An appropriate but simple medium is used in the fermentation.

The preferred carbon source consists solely of glucose and the nitrogen source consists of yeast powder (7% N content).

The C/N molar ratio is maintained at 7 to 8.

The nitrogen and carbon sources are sterilized separately and added separately.

The nitrogen source is supplied all at once at the beginning of the glucose fermentation and is added in "fed batch" mode.

The culture medium is water which contains:

the antifoam (based on food-grade silicone) and/or sunflower oil for controlling the level of foam produced and
sodium hydroxide (NaOH) for controlling the pH at an optimum value between 6.5 and 7.1.

The optimum temperature is preferably 27 to 28° C.

The medium is stirred during the fermentation.

This is carried out by means of aeration produced by "sparging" sterilized air into the medium, which provides the cells with oxygen.

The aeration is not controlled and is kept at a maximum throughout the fermentation at a value between 0.8 and 1 VVM.

There is no additional mechanical stirring to promote aeration.

At the end of the fermentation, when the glucose content is equal to zero and the increase in pH to more than 7.5 (which indicates the beginning of cell lysis), the reactor is stopped and the microorganisms can then be removed from the fermentation tank by means of filtration (filter-press).

During the fermentation in the 85 m$^3$ reactor, the entire amount of carbon source present in the medium is controlled and five steps were clearly identified, as described hereinafter:

1. First Step

This begins at t 0 h and generally ends after 20 to 24 hours.

During this period, the carbon source is in excess and must not be limited for the growth of the cells.

The carbon source is not added during this period and the content of reducing sugars in the medium decreases from 30 to 20 g/l.

The pH is not controlled: its value decreases slightly from 6.3 to 5.7.

At the end of this first step, the concentration of biomass can reach 16 g/l of medium, the total lipid content is at least 4.7 g/l of medium, and the arachidonic acid content is preferably more than 1.3 g/l of medium.

2. Second Step

This begins at t=20 hours and generally ends after 50 to 55 hours.

During this period, the available carbon source must not be limited and the speed of addition should normally be slightly less than the rate of consumption by the cells.

A glucose solution (25 g/l) is added at an average rate of 0.15 M of carbon/kg of medium per hour (the unit is a molar amount of carbon in the carbon source) and the content of reducing sugars in the medium decreases from 20 to 11 g/l.

The pH is adjusted and controlled from 5.7 to 7 by feeding with a solution of NaOH.

At the end of this second step, the concentration of biomass can reach 21 g/l of medium, the total lipid content is at least 8.3 g/l of medium, and the arachidonic acid content is preferably more than 3.1 g/l of medium.

The objective of these first two steps is to produce the main amount of biomass.

3. Third Step

This begins at t=55 hours and generally ends after 100 to 105 hours.

During this period, the available carbon source is still not limited and the speed of addition should normally be less than the rate of consumption by the cells.

A glucose solution (25 g/l) is added at an average rate of 0.08 M/kg of medium per hour and the content of reducing sugars decreases from 11 to 4 g/l.

The pH is adjusted and controlled at a value from 7 to 7.1 by adding a solution of NaOH.

At the end of this third step, the concentration of biomass can reach 24 g/l, the total lipid content is at least 11 g/l, and the arachidonic acid content is preferably more than 5 g/l of medium.

4. Fourth Step

This begins at t=100 hours and generally ends after 130 to 135 hours.

During this period, the carbon source is slightly limited and the speed of addition should normally be less than the rate of consumption by the cells.

A glucose solution (25 g/l) is added at an average rate of 0.04 M of carbon/kg of medium per hour and the content of reducing sugars decreases from 4 to 1 g/l.

The pH is not controlled and increases slightly, going from 7.1 to 7.3.

At the end of this fourth step, the concentration of biomass can reach 26 g/l of medium, the total lipid content is at least 12.4 g/l of medium, and the arachidonic acid content is preferably more than 6.2 g/l of medium.

The objective of the third and fourth steps is to produce the main amount of lipids.

5. Fifth Step

This begins at t=130 hours and generally ends after 160 to 170 hours.

During this period, the available carbon source is limited and the supply of carbon source is stopped.

The content of reducing sugars in the medium decreases rapidly from 1 to 0 g/l.

The pH is not controlled and increases slightly from 7.3 to 7.5.

At the end of this fifth step, the concentration of biomass can reach 27 g/l of medium, the total lipid content is at least 14 g/l, and the arachidonic acid content is preferably more than 7.6 g/l of medium.

The objective of this fifth step is to increase the arachidonic acid content without affecting the total concentration of lipids.

When the pH exceeds 7.5, which indicates the beginning of cell lysis, the reactor is stopped, the fermentation medium is pasteurized for 30 minutes at 70° C., and, after cooling to 30° C.-25° C., the microorganisms are removed from the fermentor by passing them through a filter press.

The principal indicators of this conducting of the fermentation are presented in Table I below:

TABLE I

| | Steps | | | | | | | | | | | |
|---|---|---|---|---|---|---|---|---|---|---|---|---|
| | 1 | | | | 2 | | | | 3 | | | |
| Time (hours) | 0 | 8 | 16 | 24 | 32 | 40 | 48 | 56 | 64 | 72 | 80 | 88 |
| pH | 6.3 | 6.1 | 5.7 | 6.4 | 6.8 | 7.0 | 7.1 | 7.1 | 7.2 | 7.1 | 7.1 | 7.2 |
| DO (%) | 1.0 | 0.8 | 0.8 | 0.8 | 0.7 | 0.8 | 0.8 | 0.8 | 0.7 | 0.7 | 0.7 | 0.7 |
| RS (%) | 3.12 | 2.77 | 2.53 | 1.94 | 1.51 | 1.34 | 1.17 | 1.10 | 0.85 | 0.74 | 0.74 | 0.48 |
| Biomass (g/l) | Nd | Nd | Nd | Nd | Nd | 16.1 | Nd | Nd | 20.7 | Nd | Nd | 23.5 |
| TL (g/l) | Nd | Nd | Nd | Nd | Nd | 4.7 | Nd | Nd | 8.3 | Nd | Nd | 10.2 |
| ARA (g/l) | Nd | Nd | Nd | Nd | Nd | 1.3 | Nd | Nd | 3.1 | Nd | Nd | 4.3 |

TABLE I-continued

| | Steps | | | | | | | | |
|---|---|---|---|---|---|---|---|---|---|
| | 3 | | | 4 | | | 5 | | |
| Time (hours) | 96 | 104 | 112 | 120 | 128 | 136 | 144 | 152 | 160 |
| pH | 7.1 | 7.2 | 7.3 | 7.3 | 7.3 | 7.4 | 7.6 | 7.5 | 7.5 |
| DO (%) | 0.7 | 0.7 | 0.8 | 0.8 | 0.8 | 0.9 | 0.9 | 0.9 | 0.9 |
| RS (%) | 0.43 | 0.31 | 0.25 | 0.16 | 0.14 | 0.12 | 0.08 | 0.03 | 0.02 |
| Biomass (g/l) | Nd | Nd | 24.3 | Nd | Nd | 25.6 | Nd | Nd | 27.3 |
| TL (g/l) | Nd | Nd | 10.9 | Nd | Nd | 12.4 | Nd | Nd | 13.8 |
| ARA (g/l) | Nd | Nd | 5.0 | Nd | Nd | 6.2 | Nd | Nd | 7.6 |

Nd: not determined.

The results of this fermentation are given in Table II below.

TABLE II

| Average result measured on 10 batches of 85 m³ | |
|---|---|
| Duration of fermentation | 165 hours |
| Final volume | 62 m³ |
| Lipid content | 12.3 g/l |
| ARA content | 55% |
| EPA content | 0.1% |
| Crude ARA productivity | 0.04 g/l/h |

EXAMPLE 2

Recovery and Conditioning of the CNCM I-4642 Strain Biomass

At the end of the fifth step of the conducting of fermentation of example 1, after the medium has been pasteurized for 30 minutes at 70° C. and after cooling to 30-25° C., the microorganisms can then be recovered from the fermentation medium after mechanical dehydration by filtration under a press.

After filtration and washing with clean water (0.5 V of water/1 V of medium), the dry matter content of the biomass cake is 65% to 75%.

In a second step, the biomass cake is granulated into particles of 0.5 to 1.5 cm², and then the particles are dried using a fluidized bed drier.

The drying time is approximately 45 to 55 minutes with an input temperature for the air introduced at 150° C.

When the output air temperature exceeds 95 to 100° C., the air input is stopped.

The biomass is cooled to ambient temperature and the biomass is stored in 25 kg bags under nitrogen to limit oxidation.

The composition of the biomass is given in Table III below.

TABLE III

| Average result on 10 batches of 85 m³ | |
|---|---|
| Dry biomass (kg) | 1650 |
| | (98% recovery yield) |
| Moisture content (%) | 6 |
| Total lipids (g/100 g) | 44 |
| | (682 kg/batch) |
| ARA (%) | 52 |
| | (355 kg/batch) |

EXAMPLE 3

Extraction of the Crude Oil from the Dried and Granulated Biomass

The technique consists of extracting the oil by affinity with a liquid solvent.

The oil is extracted from the granules obtained in example 2 using liquid butane under a pressure of 6 to 7 bar.

In order to optimize the extraction yield, the biomass is mixed successively seven times with recycled fresh solvent, and each time the contact time is 50 to 60 min.

The extraction yield is more than 85% (and can reach values of between 90% and 95%).

The oil is recovered after vacuum distillation of the solvent and drying (pressure of 0.1 mPa and temperature of 70 to 80° C.)

Table IV below gives the profile of the crude oil obtained.

TABLE IV

| Average result on 10 batches of 85 m³ | |
|---|---|
| Extraction yield (%) | 86 |
| Moisture content (%) | 0.1 |
| Total lipids (g/100 g) | 99.9 |
| | (585 kg/batch) |
| Triglycerides (% by weight) | 87 to 93 |
| Saturated fatty acids (% by weight) | 20 to 23 |
| ARA (%) | 52 |
| | (304 kg/batch) |
| Acidity (mg KOH/g) | 2 |
| Peroxide index (meq/kg) | 5.5 |
| Unsaponifiable content (%) | 5.3 |
| Phosphorus (ppm) | <100 |
| EPA (%) | 0 |

EXAMPLE 4

Refining and Purification of the Oil

1. Refining Phase
   This refining phase comprises six successive steps conventionally carried out by those skilled in the art:
   degumming: acidification with citric acid,
   saponification: neutralization with alkalis,
   centrifugation to remove the gums and soaps,
   washing with water,
   discoloring with siliceous earth, active carbon and clay, and
   filtration.
2. Purification Phase
   The objective of the purification phase is to remove bad tastes and peroxides, and optimize the stability of the oil.

This phase successively comprises one or two steps of:

molecular distillation (used if the UNS factor is too high), and vapor deodorization under a strong vacuum.

Over the whole process, the purification yield is about 78 to 80%, and the performance indicators are presented in Table V below:

TABLE V

| Average result on 10 batches of 85 m³ | |
|---|---|
| Refining yield (%) | 79 |
| Moisture content (%) | ≤0.01 |
| Total lipids (g/100 g) | 99.99 |
|  | (462 kg/batch) |
| Triglycerides (% by weight) | ≥90 |
| Saturated fatty acids (% by weight) | 20 to 23 |
| ARA (%) | ≥50 |
|  | (231 kg/batch) |
| Acidity (mg KOH/g) | ≤1 |
| Peroxide index (meq/kg) | ≤2 |
| Unsaponifiable content (%) | ≤3 |
| Moisture content + volatile material (%) | ≤0.1 |
| Impurities (%) | ≤0.1 |
| Residual solvent (ppm) | <1 |
| PUFAs (%) | ≥65 |
| EPA (%) | 0 |
| Trans FAs (wt %) | <1 |

PUFAs: Polyunsaturated Fatty Acids
Trans FAs: Trans Fatty Acids

The final oil is in the form of a clear yellow liquid at 40° C., which is homogeneous and contains no foreign impurities.

The odor is neutral, with no rancid flavor.

The volatile fraction from the step of vapor deodorization under a strong vacuum is also recovered.

Conventionally, this deodorization step is carried out in a specific reactor, where the oil is heated and subjected to a strong vacuum in order to release the volatile fraction.

This batch technique is implemented here in a 1200 l reactor with an amount of feedstock of 50%, under an inert nitrogen atmosphere.

The oil is gradually heated from the ambient temperature to 185° C. (temperature brought about by the jacket and by an internal injection of vapor at 190° C.)

After stabilization of the temperature at 185° C., the vacuum is gradually produced up to 260 Pa and maintained for 30 minutes.

The gas fraction released by this treatment is condensed at the ambient temperature and collected by an external cyclone.

The composition of this fraction is determined by:

infrared and proton NMR spectrometries at 25° C. in solution in $CDCL_3+CD_3OD$ and phosphorus NMR spectrometry at 25° C. in solution in $CDCL_3+CD_3OD+$ buffer pH 7, and gas chromatography according to F-CPG-043 for total fatty acids.

The fraction consists predominantly of triglycerides (content estimated at approximately 80%), with squalene being detected in an amount of 10%.

The fatty acid profile is the following:

|  | ABBREVIATED NOMENCLATURE | | g/100 g |
|---|---|---|---|
| NOMENCLATURE | Chemistry | Physiology | crude |
| lauric | C12:0 |  | <0.1 |
| myristic | C14:0 |  | <0.3 |
| pentadecylic | C15:0 |  | <0.1 |
| palmitic | C16:0 |  | 5.6 |
| palmitoleic | C16:1 Δ9c |  | <0.3 |
| stearic | C18:0 |  | 8.5 |
| oleic | C18:1 Δ9c | n-9 (w9) | 7.0 |
| linoleic (LA) | C18:2 Δ9c, 12c | n-6 (w6) | 9.3 |
| γ-linolenic (GLA) | C18:3 Δ6c, 9c, 12c | n-6 (w6) | 2.1 |
| α-linolenic (ALA) | C18:3 Δ9c, 12c, 15c | n-3 (w3) | <0.3 |
| arachidic | C20:0 |  | 0.9 |
| stearidonic (SDA, STD) | C18:4 Δ6c, 9c, 12c, 15c | n-3 (w3) | <0.1 |
| gondoic | C20:1 Δ11c | n-9 (w9) | <0.3 |
| dihomo-gamma-linolenic acid (DGLA) | C20:3 Δ8c, 11c, 14c | n-6 (w6) | 1.6 |
| arachidonic (AA) | C20:4 Δ5c, 8c, 11c, 14c | n-6 (w6) | 39.2 |
| (ETE) | C20:3 Δ11c, 14c, 17c | n-3 (w3) | <0.1 |
| behenic | C22:0 |  | 1.7 |
| timnodonic (EPA) | C20:5 Δ5c, 8c, 11c, 14c, 17c | n-3 (w3) | <0.3 |
| lignoceric | C24:0 |  | 2.1 |
| (Osbond acid) | C22:5 Δ4c, 7c, 10c, 13c, 16c | n-6 (w6) | <0.1 |
| nervonic | C24:1 Δ15c | n-9 (w9) | <0.1 |
| clupanodonic (DPA) | C22:5 Δ7c, 10c, 13c, 16c, 19c | n-3 (w3) | <0.1 |
| cervonic (DHA) | C22:6 Δ4c, 7c, 10c, 13c, 16c, 19c | n-3 (w3) | <0.1 |
|  | others |  |  |
|  | total |  | 78.5 |

Limit of quantification: 0.3%/crude

Limit of detection: 0.1%/crude

EXAMPLE 5

Comparative Study of the Lipid Profile of the Oil in Accordance with the Invention in Comparison with Those of Commercial Oils or Oils Described in the Literature The fatty acids were determined by gas chromatography in the form of methyl esters after transesterification with methanolic hydrochloric acid and extraction with chloroform. The results are expressed as % distribution; the analysis is carried out by the internal standardization method.

A chromatograph (Varian 3800) equipped with a split-splitless injector with a tap focus liner and a flame ionization detector was used.

An internal standard solution containing about precisely 0.5 mg of methyl heptadecanoate per ml of methanol was prepared. The methyl heptadecanoate served as a chromatographic point of reference.

About precisely 30 mg of pre-dried sample were weighed into a 6 ml tube. 1 ml of the internal standard solution and then 2 ml of 3N methanolic hydrochloric acid were added using a pipette with two measurement lines. The tube was then stoppered and placed in a dry bath thermostated at 110° C. for 4 h.

After cooling, about 0.5 ml of water and 0.5 ml of saturated aqueous sodium chloride solution were added, and the extraction was carried out with three times 1 ml of chloroform. The chloroform phases were recovered in a 6 ml tube with them being dried on a column containing sodium sulfate. They were concentrated under a nitrogen stream to about 1 ml and injected.

The % distribution of each fatty acid (i) was obtained by the ratio of the area of the peak of this fatty acid relative to the sum of the areas of all the peaks pinpointed on the chromatogram, from lauric acid (C12:0) to DHA (C22:6 Δ4c, 7c, 10c, 13c, 16c, 19c) inclusive, with the methyl heptadecanoate peak being excluded.

The oils analyzed according to this method (in Table VI below), besides those of the invention, are oils sold by the companies Cargill, Fuxing and Suntory.

The fatty acid profiles of the oils extracted from *M. carmagensis* and *M. schmuckeri* described in the literature are present as a control.

The arachidonic acid-rich oils in accordance with the invention contain:
more than 50% of ARA,
an EPA content of about 0.1%, and
especially, compared with the other oils derived from commercial microorganisms or described in the literature, less than 0.5%, preferably less than 0.2% of myristic acid (C14:0), less than 9%, preferably less than 7% of palmitic acid (C16:0), less than 3%, preferably less than 2.5% of behenic acid (C22:0) and less than 3%, preferably less than 2.5% of lignoceric acid (C24:0).

| Fatty acid codification | Oil extracted from the CNCM I-4642 strain | Cargill | Fuxing | Suntory | EP 726321 M. schmuckeri % area | EP 726321 M. camargensis − CSL | EP 726321 M. camargensis + CSL |
|---|---|---|---|---|---|---|---|
| Myristic acid C14:0 | 0.1 | 0.4 | 0.3 | 0.4 | 0.3 | 0.5 | 0.5 |
| Palmitic acid C16:0 | 6.7 | 6.8 | 7.5 | 12.3 | 13.5 | 19.7 | 16.7 |
| Palmitoleic acid C16:1 | 0.3 | | 0.4 | 0.08 | 0.6 | 0.4 | 0.3 |
| Stearic acid C18:0 | 10.0 | 6.1 | 5.1 | 7.9 | 8.0 | 4.9 | 8.4 |
| Oleic acid C18:1 | 8.6 | 5.6 | 3.3 | 6.1 | 11.8 | 17.0 | 7.8 |
| Linoleic acid (LA) C18:2 | 9.3 | 8.3 | 2.8 | 9.0 | 10.8 | 14.2 | 14.3 |
| γ-linolenic acid (GLA) C18:3 | 2.6 | 2.3 | 2.7 | 2.3 | 4.1 | 6.0 | 7.7 |
| Arachidic acid C20:0 | 1.2 | ND | 0.8 | 0.8 | ND | ND | ND |
| Gondoic acid C20:1 | 0.5 | ND | 0.3 | 0.4 | 0.3 | 0.9 | 0.4 |
| Eicosadienoic acid C20:2 | 0.5 | ND | 0.5 | 0.7 | 0.6 | 0.5 | 0.9 |
| Dihomo-gamma-linolenic acid C20:3 | 1.8 | 3.8 | 4.2 | 0.6 | 0.5 | 2.2 | 0.5 |
| Arachidonic acid C20:4 | 50.4 | 41.3 | 48.3 | 46.2 | 40.3 | 24.7 | 30.0 |
| Timnodonic acid (EPA) C20:5 | 0.1 | 0.2 | 0.1 | ND | ND | 0 | 0.1 |
| Behenic acid C22:0 | 2.4 | 3.3 | 3.5 | 3.0 | 5.2 | 3.6 | 7.8 |
| Lignoceric acid C24:0 | 2.3 | 9.8 | 10.8 | 8.2 | 2.8 | 4.4 | 3.8 |

ND: Not detected

EXAMPLE 6

Characterization of the Residual Biomass Obtained after the Oil Extraction Step After the refining and purification steps of example 4, the residual biomass obtained has a dry matter content of between 85% and 95%.

Analyses are then carried out in order to determine the content thereof of:

total nitrogen (determination of the % of N 6.25),
total lipids,
total sugars, and
soluble fibers,
and also:
the residual fatty acid distribution,
the residual sugar profile, and
the aminogram.

Table VII below gives the profiles of five batches of residual biomass.

| ARA biomass | Units | batch 1 | batch 2 | batch 3 | batch 4 | batch 5 |
|---|---|---|---|---|---|---|
| Dry matter | % | 87.60 | 90.90 | 91.20 | 91.70 | 90.90 |
| N × 6.25 | %/crude | 33.80 | 36.20 | 37.30 | 36.50 | 36.50 |
| Calcination residue | %/crude | 4.50 | 4.70 | 4.80 | 4.60 | 4.70 |
| Total lipids | %/crude | 12.10 | 12.10 | 11.50 | 11.80 | 12.70 |
| Fibers (PROSKY method) | %/crude | 23.20 | 23.00 | 25.00 | 26.40 | 24.10 |
| Fatty acid profile | | | | | | |
| C12:0 lauric | %/crude | <0.03 | <0.03 | <0.03 | <0.03 | <0.03 |
| C14:0 myristic | %/crude | <0.1 | <0.1 | <0.1 | <0.1 | <0.1 |
| C15:0 pentadecylic | %/crude | <0.03 | <0.03 | <0.03 | <0.03 | <0.03 |
| C16:0 palmitic | %/crude | 1.40 | 1.40 | 1.20 | 1.40 | 1.40 |
| C16:1 Δ9c palmitoleic | %/crude | 0.20 | 0.20 | 0.20 | 0.20 | 0.20 |
| C18:0 stearic | %/crude | 1.00 | 1.10 | 1.00 | 1.10 | 1.10 |
| C18:1 Δ9c oleic | %/crude | 1.10 | 1.20 | 0.90 | 1.20 | 1.20 |
| C18:2 Δ9c, 12c linoleic (LA) | %/crude | 0.90 | 1.00 | 0.80 | 1.00 | 0.90 |
| C18:3 Δ9c, 12c, 15c a-linolenic (ALA) | %/crude | <0.03 | <0.03 | <0.03 | <0.03 | <0.03 |
| C18:3 Δ6c, 9c, 12c g-linolenic (GLA) | %/crude | 0.50 | 0.50 | 0.40 | 0.50 | 0.50 |
| C18:4 Δ6c, 9c, 12c, 15c stearidonic (SDA, STD) | %/crude | <0.03 | <0.03 | <0.03 | <0.03 | <0.03 |
| C20:0 arachidic | %/crude | <0.1 | <0.1 | <0.1 | <0.1 | <0.1 |
| C20:1 Δ11c gondoic | %/crude | <0.1 | <0.1 | <0.1 | <0.1 | <0.1 |
| C20:3 Δ8c, 11c, 14c dihomo-g-linolenic (DGLA) | %/crude | 0.30 | 0.30 | 0.30 | 0.30 | 0.30 |
| C20:3 Δ11c, 14c, 17c (ETE) | %/crude | <0.03 | <0.03 | <0.03 | <0.03 | <0.03 |
| C20:4 Δ5c, 8c, 11c, 14c arachidonic (AA) | %/crude | 4.40 | 4.00 | 4.50 | 3.80 | 4.20 |
| C20:5 Δ5c, 8c, 11c, 14c, 17c timnodonic (EPA) | %/crude | <0.03 | <0.03 | <0.03 | <0.03 | <0.03 |
| C22:0 behenic | %/crude | 0.20 | 0.20 | 0.20 | 0.20 | 0.20 |
| C22:5 Δ7c, 10c, 13c, 16c, 19c clupanodonic (DPA) | %/crude | <0.03 | <0.03 | <0.03 | <0.03 | <0.03 |
| C22:5 Δ4c, 7c, 10c, 13c, 16c (Osbond acid) | %/crude | <0.03 | <0.03 | <0.03 | <0.03 | <0.03 |
| C22:6 Δ4c, 7c, 10c, 13c, 16c, 19c cervonic (DHA) | %/crude | <0.03 | <0.03 | <0.03 | <0.03 | <0.03 |
| C24:0 lignoceric | %/crude | 0.40 | 0.40 | 0.40 | 0.40 | 0.40 |
| C24:1 Δ15c nervonic | %/crude | <0.03 | <0.03 | <0.03 | <0.03 | <0.03 |
| Other fatty acids | %/crude | 0.10 | 0.10 | 0.10 | 0.10 | 0.10 |
| Σ TGA | %/crude | 10.60 | 10.50 | 10.00 | 10.30 | 10.60 |
| Sugar profile | | | | | | |
| Arabinose | %/crude | <0.1 | <0.1 | <0.1 | <0.1 | <0.1 |
| Galactose | %/crude | 1.20 | 1.00 | 1.00 | 1.10 | 1.10 |
| Glucose | %/crude | 13.50 | 15.90 | 15.00 | 16.10 | 15.10 |
| Mannose | %/crude | 1.70 | 1.80 | 1.90 | 1.80 | 1.90 |
| Rhamnose | %/crude | nd | nd | nd | nd | nd |
| Ribose | %/crude | 0.30 | 0.30 | 0.30 | 0.30 | 0.30 |
| Xylose | %/crude | 0.10 | 0.10 | 0.10 | 0.10 | 0.10 |
| Σ total sugars | %/crude | 16.80 | 19.10 | 18.30 | 19.40 | 18.50 |
| Aminogram | | | | | | |
| Aspartic acid | %/crude | 2.06 | 2.34 | 2.41 | 2.42 | 2.35 |
| Glutamic acid | %/crude | 2.82 | 3.15 | 3.13 | 3.19 | 3.06 |
| Alanine | %/crude | 1.40 | 1.56 | 1.44 | 1.58 | 1.48 |
| Arginine | %/crude | 1.68 | 2.00 | 2.39 | 1.98 | 2.21 |
| Cystine | %/crude | 0.39 | 0.43 | 0.48 | 0.44 | 0.45 |
| Glycine | %/crude | 1.07 | 1.23 | 1.16 | 1.21 | 1.17 |
| Histidine | %/crude | 1.08 | 1.24 | 1.21 | 1.23 | 1.13 |
| Isoleucine | %/crude | 0.94 | 1.06 | 0.99 | 1.05 | 1.01 |
| Leucine | %/crude | 2.40 | 2.78 | 3.12 | 2.73 | 2.71 |
| Lysine | %/crude | 2.05 | 2.38 | 2.39 | 2.34 | 2.31 |
| Methionine | %/crude | 0.49 | 0.51 | 0.44 | 0.47 | 0.45 |
| Phenylalanine | %/crude | 1.64 | 1.90 | 2.03 | 1.87 | 1.81 |
| Proline | %/crude | 0.89 | 1.02 | 1.07 | 1.10 | 1.08 |

-continued

| ARA biomass | Units | batch 1 | batch 2 | batch 3 | batch 4 | batch 5 |
|---|---|---|---|---|---|---|
| Serine | %/crude | 1.10 | 1.27 | 1.28 | 1.27 | 1.25 |
| Threonine | %/crude | 1.17 | 1.29 | 1.31 | 1.32 | 1.30 |
| Tryptophan | %/crude | 0.65 | 0.69 | 0.93 | 0.71 | 0.74 |
| Tyrosine | %/crude | 0.87 | 0.96 | 1.05 | 1.00 | 1.01 |
| Valine | %/crude | 1.33 | 1.47 | 1.53 | 1.48 | 1.46 |
| Σ TAA | %/crude | 24.00 | 27.30 | 28.40 | 27.40 | 27.00 |
| Heavy metal content | | | | | | |
| Lead | mg/kg | 0.04 | 0.04 | 0.05 | 0.04 | 0.03 |
| Cadmium | mg/kg | 0.06 | 0.07 | 0.07 | 0.06 | 0.07 |
| Mercury | mg/kg | <0.01 | <0.01 | <0.01 | <0.01 | <0.01 |
| Arsenic | mg/kg | 0.12 | 0.11 | 0.11 | 0.11 | 0.11 |
| Zinc | mg/kg | 22 | 23 | 23 | 22 | 25 |
| Chromium | mg/kg | 8.9 | 2 | 1.4 | 1.2 | 2 |
| Manganese | mg/kg | 6.8 | 6.9 | 6.9 | 6.6 | 7 |

The residual biomass therefore appears to be absolutely suitable for the application thereof in animal feed, both by virtue of its protein nitrogen content (between 35% and 45%), its soluble fiber content (between 20% and 30%) and its residual sugar content (between 15% and 20%) and, for certain specific species (pets, aquaculture), by virtue of its residual ARA content (between 3.5% and 4.5%).

The invention claimed is:

1. A method for producing lipid compounds of interest, comprising culturing a strain of *Mortierella alpina* and recovering biomass rich in lipid compounds of interest and, optionally, harvesting the lipid compounds of interest, said strain of *Mortierella alpina* being the *Mortierella alpina* strain deposited on Jun. 12, 2012, with the Collection Nationale de Cultures de Microorganismes (CNCM) under accession number I-4642 or a mutagenized or genetically transformed strain of the *Mortierella alpina* strain deposited on Jun. 12, 2012, with the Collection Nationale de Cultures de Microorganismes (CNCM) under accession number I-4642 retaining the property of producing at least 50% arachidonic acid (ARA) by weight of total fatty acids,
wherein the recovered biomass has between 40% and 55% by weight of lipids and at least 50% arachidonic acid by weight of total fatty acids.

2. The method according to claim 1, wherein the lipid compound of interest is arachidonic acid (ARA).

3. The method according to claim 2, wherein the arachidonic acid (ARA) is harvested and/or extracted as an oil with arachidonic acid (ARA).

4. The method according to claim 3, characterized in that the oil containing the arachidonic acid (ARA) is prepared by means of a method comprising:
culturing the strain under heterotrophic conditions so as to produce a biomass having between 40% and 55% by weight of lipids and between 50% and 55% by weight of arachidonic acid (ARA) relative to total fatty acids,
harvesting the biomass thus prepared,
drying said biomass,
extracting the oil with a solvent chosen from the group consisting of hexane and butane, more particularly with liquid butane, and
refining and recovering the oil thus extracted.

5. The method according to claim 1, wherein said strain of *Mortierella alpina* is the *Mortierella alpina* strain deposited on Jun. 12, 2012, with the Collection Nationale de Cultures de Microorganismes (CNCM) under accession number I-4642.

6. The method according to claim 1, wherein said strain of *Mortierella alpina* is a mutagenized or genetically transformed strain of the *Mortierella alpina* strain deposited on Jun. 12, 2012, with the Collection Nationale de Cultures de Microorganismes (CNCM) under accession number I-4642 that retains the property of producing at least 50% arachidonic acid (ARA) by weight of total fatty acids.

* * * * *

UNITED STATES PATENT AND TRADEMARK OFFICE
CERTIFICATE OF CORRECTION

PATENT NO. : 9,476,075 B2  Page 1 of 1
APPLICATION NO. : 14/428077
DATED : October 25, 2016
INVENTOR(S) : Qian It is certified that error appears in the above-identified patent and that said Letters Patent is hereby corrected as shown below:

In the Claims

Column 2,
Line 15, delete "bonds, all the" and insert --bonds, "all" the--.

Column 9,
Line 13, delete "t 0 h" and insert --t = 0 h--.

Signed and Sealed this
Twenty-first Day of February, 2017

Michelle K. Lee
*Director of the United States Patent and Trademark Office*

SEQUENCE LISTING

<160> NUMBER OF SEQ ID NOS: 1

<210> SEQ ID NO 1
<211> LENGTH: 361
<212> TYPE: DNA
<213> ORGANISM: Mortierella alpina

<400> SEQUENCE: 1

```
ttaaacagtg cgtgaaattg ttgaaaggga aacgcttgac accagtcatg cgagcggaaa      60
atcagtctTT tgcagtgggg agttgtgtgg gttcggaccg caaggccggc ctgtgctgca     120
tctctgctgt aagtgatgca cttttTCgtt tgcaggccaa catcagtttc ttctgctgga     180
caaaactctt gagaaggtag cagctttggc tgtgttatag ctcttgagcg atacagtgga     240
ggggactgag gttttcgcag cgcgtgctct cgggcaaggc tgattgggtg ctatgggatc     300
gttcggtgta caatgcatgc attttgcgcc gtgtcttTTc tgtactcgct caactcggct     360
c                                                                    361
```